United States Patent [19]
Joie et al.

[11] Patent Number: 5,562,836
[45] Date of Patent: Oct. 8, 1996

[54] METHOD FOR STORING BLOOD IN A CONTAINER HAVING MULTIPLE CHAMBERS

[75] Inventors: Michel Joie, Ernage; Jack Debrauwere, Halle; Jean-Claude Bernes, Faimes, all of Belgium

[73] Assignee: Baxter International Inc., Deerfield, Ill.

[21] Appl. No.: 437,992

[22] Filed: May 10, 1995

Related U.S. Application Data

[62] Division of Ser. No. 241,080, May 11, 1994.

[51] Int. Cl.$^6$ ................................................ B01D 21/26
[52] U.S. Cl. ................................ 210/782; 210/789; 604/4; 604/5; 604/408; 604/410
[58] Field of Search .................................. 210/782, 789, 210/767; 422/1; 604/4, 5, 6, 408, 410

[56] References Cited

U.S. PATENT DOCUMENTS

| | | | |
|---|---|---|---|
| 3,987,961 | 10/1976 | Sinn et al. | 604/410 |
| 4,350,585 | 9/1982 | Johansson et al. | 210/94 |
| 4,608,178 | 8/1986 | Johansson et al. | 210/744 |
| 4,820,297 | 4/1989 | Kaufman et al. | 604/409 |
| 4,846,005 | 7/1989 | Bacehowski et al. | 73/864.81 |
| 4,900,321 | 2/1990 | Kaufman et al. | 604/409 |
| 5,102,407 | 4/1992 | Carmen et al. | 604/410 |
| 5,128,048 | 7/1992 | Stewart et al. | 210/767 |
| 5,180,504 | 1/1993 | Johnson et al. | 210/767 |

*Primary Examiner*—John Kim
*Attorney, Agent, or Firm*—Robert M. Barrett; Bradford R. L. Price; Joseph B. Barrett

[57] ABSTRACT

A method for separating blood into its components and individually storing same is provided. The method has the steps of: providing a container having a body with at least a first and second chamber. Selective fluid communication is also possible between the first and second chamber, and a tube is in fluid communication with the first chamber. The method also has the steps of: passing the blood into the first chamber through the tube; centrifuging the container to separate the blood into plasma, red blood cells and buffy coat within the first chamber; and expressing a portion of the centrifuged blood into the second chamber. In another embodiment, the method for storing blood has the steps of: providing a container with a body having three chambers. The method has steps that include passing the blood into a chamber through the tube; centrifuging the container to separate the blood into plasma, red blood cells and buffy coat and expressing a portion of the separated blood into second and third chambers from the collection chamber.

10 Claims, 3 Drawing Sheets

METHOD FOR STORING BLOOD IN A CONTAINER HAVING MULTIPLE CHAMBERS

This is a division of application Ser. No. 08/241,080, filed on May 11, 1994.

BACKGROUND OF THE INVENTION

The present invention generally relates to the storage of body fluids. More specifically, the present invention relates to the separation of blood into its components and the storage of blood components.

It is, of course, known to use blood and other body fluids in a number of medical procedures. Blood transfusions are an example of such procedures. Blood is collected from a donor and can be transfused into a recipient.

Blood after being received from a donor is stored, typically, in flexible plastic containers until use. Blood can either be stored in a container as whole blood or broken down into its individual components, (i.e., plasma, buffy coat layer, and packed red cells). For example, it is known to separate whole blood either through a centrifuge process, or a process such as that disclosed in U.S. Pat. Nos. 4,350,585 and 4,608,178, into plasma, buffy coat, and packed red cells.

In a great majority of cases, blood is stored for a number of days and not immediately infused into a recipient. In most situations, the blood components are separately stored. For example, it is known to separately store and utilize the red blood cell component of whole blood.

In order to maintain the viability of red blood cells and other blood components, it is necessary to provide a storage solution to provide an energy source for the red blood cells.

Previous systems of manual blood collection consist of several blood packs connected with pieces of tubing and isolated, if necessary, by frangible parts. Most of the prior art pack configurations have a similar construction with a collection bag filled with anti-coagulant solution wherein, e.g., one pack is dedicated to the storage of red blood cell concentrates mixed with the preservative solution and one transfer pack is dedicated to the processing and storage of plasma.

In a known system, marketed by Baxter International under the trademarks OPTIPRESS® and OPTIPAC®, whole blood is collected. The whole blood is then centrifuged to separate the blood into plasma, red blood cells, and a buffy coat. Plasma and red blood cells are separated by being removed from the blood pack through top and bottom tubes connected to peripheral transfer packs.

Although, the use of a triple pack configuration provides a system that can store blood components, a typical triple blood pack can present some issues. For example, the handling of a triple blood pack can be cumbersome due to the tubing becoming knotted and intertwined. Further, the pieces of tubing in the triple packs are labor intensive to manufacture and can create problems with bonding and kinking during sterilization. Furthermore, the packaging of triple packs with attached tubing can be problematic.

There therefore may be a need for an improved system for collecting and storing blood and its components.

SUMMARY OF THE INVENTION

The present invention provides an improved blood collection system. To this end, a single container is provided for separately housing blood components. The container includes a body defined by flexible walls defining at least a first, a second and a third chamber. Means are provided for allowing selective fluid communication between the first chamber and the second chamber and between the second chamber and the third chamber. The container of the present invention provides a compact tubeless system for collecting and separately storing blood components.

In use, blood can be collected in the middle or second chamber of the container. The container is then centrifuged to separate the blood into a plasma layer, a red blood cell layer, and a buffy coat layer. The upper layer will be the plasma layer, the middle layer the buffy coat layer and the lower layer the red blood cell layer. Pursuant to the present invention, the frangible connections located in the tubes between the first and second chamber and second and third chamber, can be separated and the bottom layer expressed into the first chamber and the top layer expressed into the third chamber.

In an embodiment, a blood separator is used to express the blood into the different chamber.

In an embodiment, the chambers are sealed by heat sealing the tubes after the blood components are expressed into appropriate chambers.

In an embodiment, the blood collection system has bar code labeling for identification.

In an embodiment, the present invention provides a blood separation apparatus having a means for sensing levels of blood and its components. In an embodiment, the blood separation apparatus has an optical sensor.

In an embodiment, the container has a plurality of mounting holes for securing the container to the blood separation apparatus.

An advantage of the present invention is that it provides an improved container for housing blood components.

Another advantage of the present invention is that it provides a blood collection system that reduces the manufacturing costs by providing the capability for high volume, highly automated production.

Moreover, an advantage of the present invention is that it provides an improved method for storing blood components.

Further, an advantage of the present invention is that it provides a blood collection system having improved handling characteristics.

Still further, an advantage of the present invention is that it provides a blood collection system that does not include a plurality of tubing.

Another advantage of the present invention is that it provides several channels of separated blood for later analysis. Moreover, an advantage of the present invention is that it provides a blood collection system with improved labeling features for better traceability and safety.

Another advantage of the present invention is to provide an apparatus for improved blood separation.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an apparatus and method for separating and storing blood components in separate chambers. As used herein, the term "blood" includes whole blood as well as its components including, but not limited to, red blood cells, plasma, platelets, and leukocytes (i.e., buffy coat).

Figure 1:
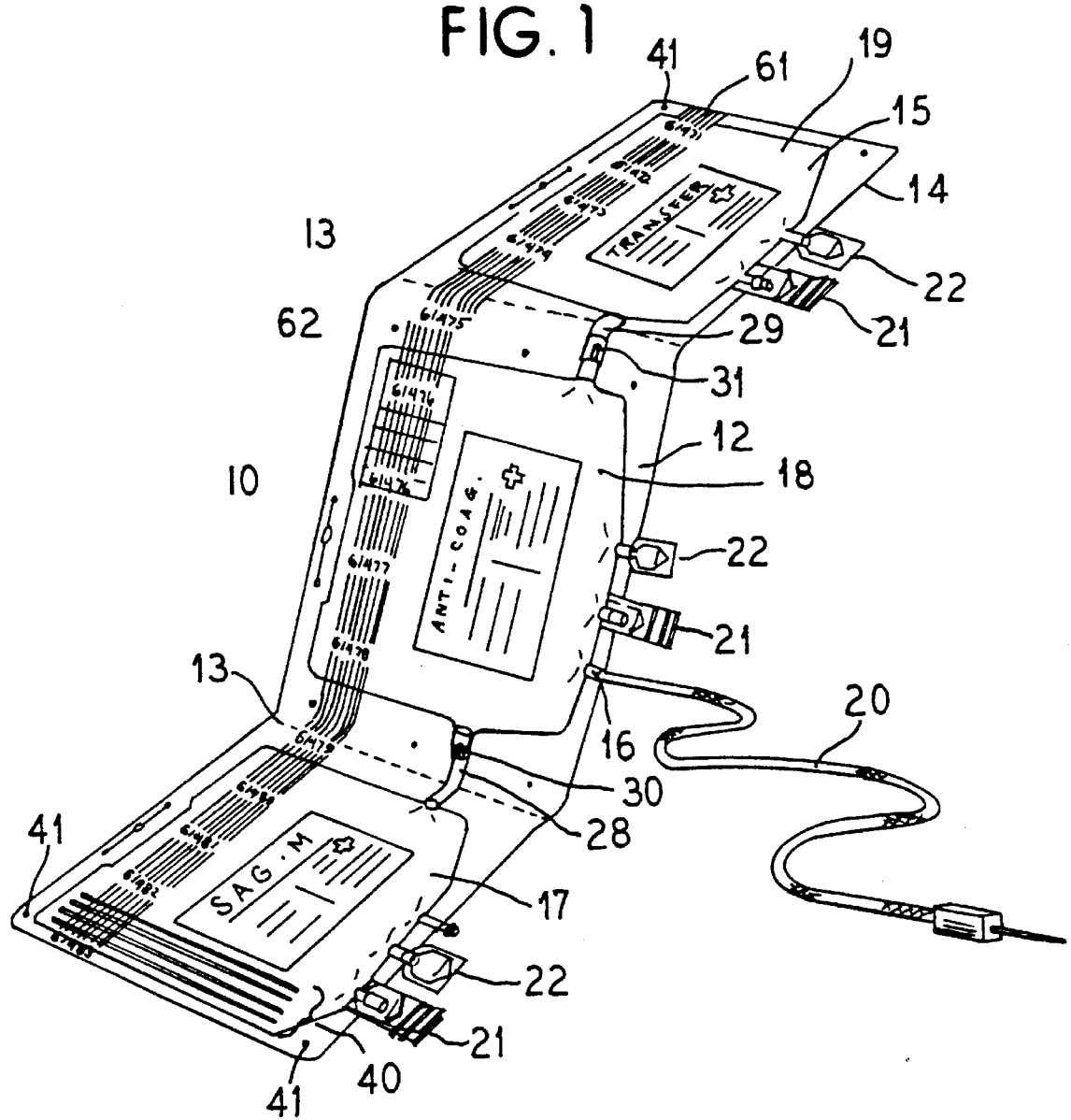
FIG. 1 illustrates a perspective view of a container of the present invention.

Pursuant to the present invention, an integral container is provided for collecting, separating, and storing blood components. Referring now to the figures, FIG. 1 illustrates the blood collection system of the present invention. Preferably the container includes a body made of flexible material (i.e., PVC or other suitable material). The body is divided into multiple chambers that can house blood and separately store the blood components in the individual chambers. The chambers are also isolated by frangible access ports.

Referring specifically to an embodiment illustrated in FIG. 1, a container 10 having a body 12 is preferably constructed from flexible sheets of plastic. The sheets are sealed along their edges 14 to create an interior 15. The container 10 is divided into three chambers, namely, a first chamber 17, a second chamber 18 and a third chamber 19.

A number of plastics can be utilized. Depending on the specific components to be stored, certain plastics may be more desirable. In an embodiment, the container is constructed from a polyvinyl chloride material that is plasticized and includes stabilizers. The container material is preferably flexible to facilitate folding the container for storage. To this end, a fold line 13 is provided between each chamber of the container to facilitate folding the container for centrifuging and other processing while the blood is stored in the container.

Each chamber of the container 10 preferably includes at least one port that provides access to the interior 15 of the individual chambers. For example, a donor tube 20 is provided, through which blood can be collected into the second chamber 18 of the container. In the preferred embodiment illustrated, sterile connections sites 22 and administration ports 21 are also provided on each chamber of the container.

In order to provide means for allowing the blood components to be stored in separate compartments, at least two tube members are provided. A first tube member 28 being located between the first and second chambers 17 and 18, respectively, and a tube 29 being located between the second and third chambers 18 and 19, respectively. In order to provide selective fluid flow between the chambers, a frangible cannula 30 and 31 is located in each of the tubes 28 and 29, respectively. By breaking the appropriate frangible cannula, fluid flow between the chambers can be established. Of course, other means of establishing selective fluid communication can be used.

In the illustrated embodiment, another feature provided on each chamber of the container and illustrated in FIG. 1 is means (mounting holes) for securing the container 10 to a blood separator 50 (discussed below). In the illustrated embodiment, the mounting holes 41 are located approximately at the outer edges of the first chamber 17 and the third chamber 19. Additionally, the center chamber 18 has two sets of mounting holes 41. The mounting holes 41 are used to align the container 10 on a blood separator 50 (discussed below).

Another illustrated feature of the container is a set of segments sealing lines 40. These are located, for example, on the edge of the first chamber 17 and can be used for providing cross-matching segments. In addition to providing cross-matching segments, which aid in the identification of the blood components, the present invention advantageously provides a further identification feature, namely a donation number identifying each chamber with a bar code 61 or a number printed on the pack during manufacturing. This bar code 61 provides that the three individual packs are identifiably correlated.

Also illustrated in FIG. 1 are peelable stickers 62 with corresponding donation numbers. These stickers 62 provide labeling for the individual chambers that house the blood components and can be printed and affixed to the chambers during the manufacturing of the container. The peelable stickers 62 also provide that the three individual packs are identifiably correlated, i.e. as being from the same source. Also, the peelable stickers 62 provide for other specialized labeling functions as desired. For example, these stickers 62 provide labeling for later use on test tubes containing the donor's blood samples.

Many of the features of the preferred embodiments listed above improve and facilitate a primary purpose of the present invention, to wit, the collection, separation and storage of blood. In a preferred embodiment of the present invention, the blood is collected from the patient and enters the center or second chamber 18 of the three-chambered pack 10. To accomplish this, the donor tube 20 extends either from a donor needle or from another container containing blood. Blood then flows through the donor tube 20 into the interior 15 of the container 10. Each of the chambers is provided with an administration port 21 and a sterile connection site 22 to process the contents of the component packs by usual blood bank procedures (i.e., red cell filtration on SAG-M pack, buffy coat pooling and single donor platelet by a known PRP method). After donation is completed, the donor tube 20 is stripped and sealed to provide cross-matching segments, if necessary.

Also, after the blood has been added to the container 10 pursuant to the invention, the donor tube 20 can be severed from the container 10. A variety of methods can be used to so sever the donor tube 20 including using a heat sealer. The donor tube 20 can then be used for cross-matching purposes.

Figure 2:
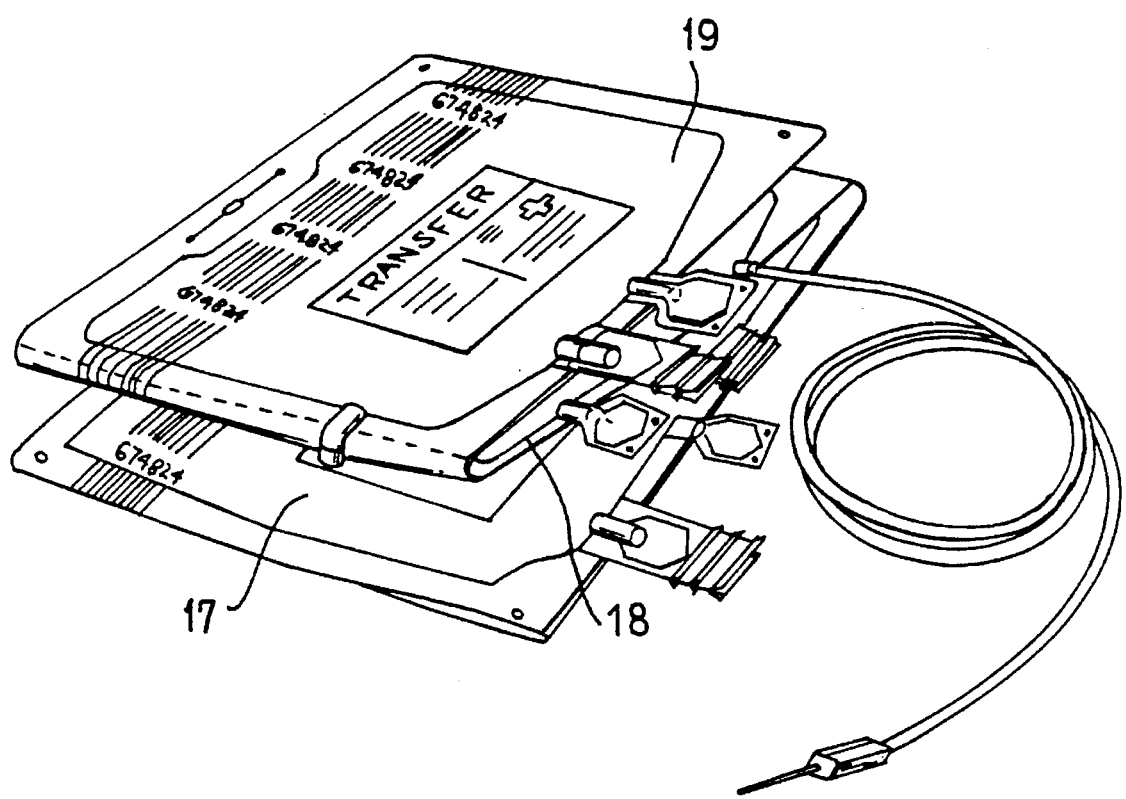
FIG. 2 illustrates the container of the present invention of FIG. 1 in a preferred folded orientation in preparation for centrifugation.

After collecting the blood, further processing can be performed, i.e., centrifugation for separating the blood into its components. To this end, the pack is folded as shown in FIG. 2 in preparation for centrifugation. First, the first chamber 17 is laid flat. Then the second chamber 18 is folded upon it along the fold line 13 between the adjacent first and second chambers. Finally, the third chamber 19 is similarly folded upon the second chamber 18 along the fold line 13 between the adjacent second and third chambers. The folded pack provides a clean, efficient package for easily handling the collected blood; no excessive tubing is present to become tangled. The folded pack is then placed in a centrifuge bucket for spinning with the sterile connection sites 22 and administrative ports 21 placed on the side of the assembly.

The centrifuge separates the collected whole blood into its components (i.e., plasma, buffy coat layer and packed red cells). The separated layers are all contained within the second chamber 18 after centrifugation; the components are stratified. The packed red cells reside nearest the fold line 13 at the junction of the first chamber 17 and the second chamber 18. The plasma resides nearest the fold line 13 at the junction of the second chamber 18 and the third chamber 19. The buffy coat is disposed between the red cells and plasma in the second chamber 18.

After centrifugation to separate the three components of the donated blood (i.e., plasma, buffy coat layer, and packed red cells), the collection system is carefully unfolded and secured to a blood component separator. The blood component separator preferably operates in a manner similar to that used in a press sold by affiliates of Baxter International under the trademark OPTIPRESS®.

Figure 3:
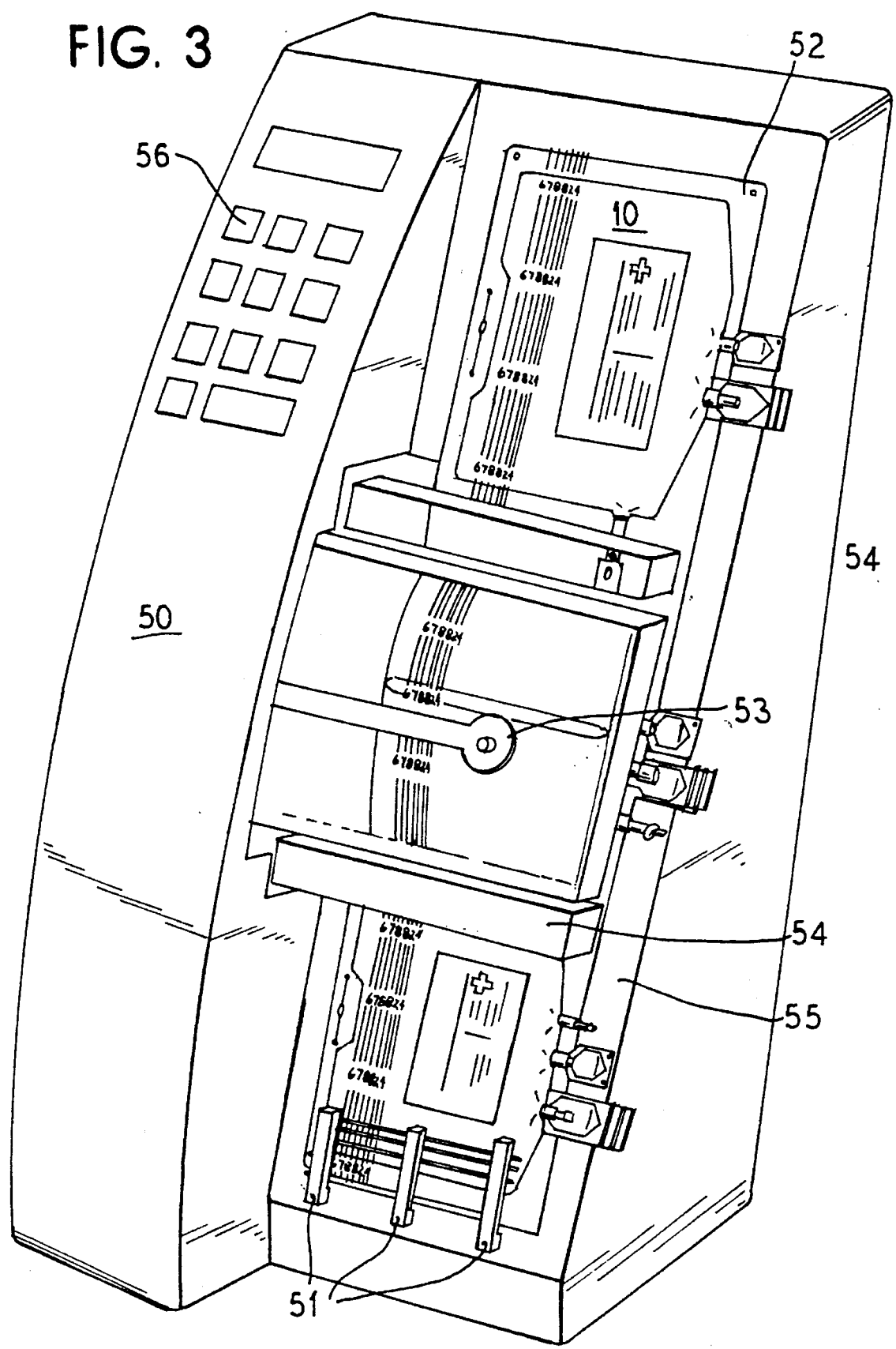
FIG. 3 illustrates an embodiment of the container of the present invention mounted in a blood separation system.

FIG. 3 is an embodiment of the invention illustrating a blood component separator apparatus 50 that can be used for separating whole blood into plasma, red blood cells, and buffy coat.

A preferred embodiment illustrated in FIG. 3 provides an automated blood component separator 50. The separator 50 has a front face 55 and a control panel 56. The operator uses this panel 56 to operate the blood component separator 50 in an automated manner. Thus, after the blood component separator 50 has been activated, the operator may leave the automated separator 50 unattended to separate the collected whole blood into its components. To accomplish this, the container 10 is secured to the front face 55 of the blood component separator 50 by using mounting pegs 52 which cooperate with the alignment mounting holes 41 on the container 10. Also shown in FIG. 3 near the base of the separator 50 is a segment sealing bar 51, which aids in holding the container 10 to the blood component separator 50.

Further elements of the blood component separator 50 include a frangible opening, sealing and cutting bar 54. This bar 54 is located at the folding seam 13 between the first chamber 17 and the second chamber 18, approximately a third of the way up the front face 55. Similarly, at the folding seam 13 between the second chamber 18 and the third chamber 19 is another similar bar 54. In addition, the frangible opening, sealing and cutting bar 54 has tools for accomplishing several tasks. For example, the bar 54 has a tool for opening the frangible cannula 30 to provide fluid communication between the adjacent chambers. These bars 54 also aid in holding the container 10.

In the preferred embodiment illustrated, in order to provide selective fluid communication between the interior 15 of one chamber and the interior 15 of another chamber of the container 10, a frangible cannula 30 is utilized. To provide fluid communication, the frangible cannula 30 is biased so that a portion thereof breaks away from the remaining portions of the cannula. This allows the fluid within one chamber to flow into the interior of an adjacent chamber of the container, for example, from the second chamber 18 to the first chamber 17. Although in the embodiment illustrated, a frangible cannula 30 is used, any means for allowing selective access between the interiors of the container can be utilized.

To this end, the frangible opening, sealing and cutting bars 54 located at the top and bottom of the center or second chamber 18 have tools designed to open the frangible cannula 30, 31 to allow fluid flow between the peripheral chambers. By using the frangible opening bar 54 to open the frangible cannula 30, fluid communication between, for example, the first chamber 17 and the second chamber 18 can occur.

With the centrifuged container 10, having the stratified layers of blood components (i.e., an upper layer of blood plasma, a center layer of buffy coat and a lower layer of red blood cells) in the center or second chamber 18, secured to the blood separator 50, the separation of the components into separate chambers may begin. The bars 54 open the cannula 30 and 31 to allow fluid communication from the second chamber 18 to the first chamber 17 and from the second chamber 18 to the third chamber 19, respectively.

The blood separator 50 is provided with appropriate means for expressing the upper plasma layer from the center or second chamber 18 through the upper cannula 31 to the empty upper or third chamber 19. Similarly, the blood separator 50 is provided with appropriate means for expressing the lower red blood cell layer from the center or second chamber 18 through the lower cannula 30 to the lower or first chamber 17. The first chamber 17 is prefilled with a preservative solution to permit extended storage of the red blood cells.

The top and bottom flows are controlled by clamps (not shown). The clamps are monitored with the optical monitoring device 53 illustrated in FIG. 3. The optical monitoring device 53 detects the levels of the blood components in the chambers. This device detects when substantially all the red blood cells have been expressed from the second chamber 18 to the first chamber 17. The optical monitoring device 53 thus activates the clamps to prevent further fluid flow. In addition, the flow of plasma from the second chamber 18 to the third chamber 19 is expressed and stopped in a similar fashion. In this embodiment, only the appropriate blood components are expressed to the appropriate peripheral chambers. As a result of the expressing of the blood components, the second chamber 18 subsequently contains only the buffy coat layer. Thus, after the completed separation, the plasma is in the third chamber 19, the buffy coat is in the collection bag; i.e., the second chamber 18 and the red blood cells are in the first chamber 17.

To this end, after the blood components transfer is completed, the top and bottom transfer channels (i.e., the tubes 28 and 29) are sealed by tools located in the same sealing and cutting bars 54. This prevents further fluid communication between the chambers.

The first and second chambers and the second and third chambers are then separated by cutting them away with a knife integrated into the sealing and cutting bars 54 or by tearing them by hand using a pre-notched folding line 13. Thus, after separation, each chamber becomes an independent pack. The three separate chambers can then be distributed to where they are needed or stored individually until required.

As shown in FIG. 1, and briefly discussed above, the container 10 has labeling on each of the chambers. In a preferred embodiment, the label is a bar code 61. The bar code is generated so that information for identifying the source of the blood is readily available. Also, for tracking and safety concerns, the bar code 61 on each individual chamber pack is correlated. Thus, if one chamber pack is found to be unusable for any reason, the other two separate chamber packs can be located simply by examining the corresponding bar code and recalling the suspect chamber packs for inspection. This benefit is especially advantageous because of its simplicity. For instance, the bar code can be printed on the three chambers individually while they are being manufactured and remain a part of a single, integral container. Thus, the possibility of human error involved in applying separate labels to these individual separated packs, as is done in present practice, is virtually nullified.

In a further embodiment, an additional processing step may be performed to aid in identification of the blood. The pre-notched cross-matching segments 40 shown on the first chamber 17 can be sealed by the segment sealing bar 51. Cross-matching segments 40 can also be integrated in the pack design by isolating channels in the first chamber 17, the SAG-M pack, for example as shown in FIG. 1. The channels in the first chamber 17 are arranged parallel to each other at the outer edge. Also, the cross-matching segments 40 are pre-notched. Further, they could be isolated by using a tube sealer or by adding a sealing segment step on the component separator. The channels could also have bar codes for identification purposes.

Now referring again to FIG. 3 with the container 10 held on the blood component separator 50, the cross-matching segments 50 are disposed near the bottom of the front face 55. Three segments sealing bars 51 mounted to the front face 55 are disposed directly above and perpendicular to the channels of the cross-matching segments 40. If desired, the segments sealing bar 51 is used to seal the pre-notched segments 40. Then, the sealed segments are cut or torn apart along the notch lines. In this manner, segments are created for cross-matching.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for storing blood comprising the steps of:

providing a container having an integral body with at least a first and a second chamber connected by a common wall, means for allowing selective fluid communication between the first and second chamber through the common wall, and a tube in fluid communication with the first chamber;

passing the blood into the first chamber through the tube;

centrifuging the container for separating the blood into plasma, red blood cells, and buffy coat within the first chamber; and expressing a portion of the centrifuged blood into the second chamber through the common wall.

2. The method for storing blood of claim 1, further comprising the step of labeling the container so that each chamber bears similar indicia.

3. The method of claim 1 wherein the tube is severed after the blood is passed into the first chamber.

4. The method of claim 1 wherein to provide fluid communication, a frangible access port is broken.

5. The method of claim 1 including the step of sterilizing the container prior to adding blood to the interior of the body.

6. The method of claim 1 including the step of folding the container prior to the centrifuging step.

7. A method for storing blood comprising the steps of:

providing a container having an integral body defined by flexible walls defining a first chamber, a second chamber and a third chamber, the chambers linearly arranged so that the first chamber has a common wall with the second chamber and the second chamber has a common wall with the third chamber, means for allowing selective fluid communication between the first chamber and the second chamber and between the second chamber and the third chamber through the respective common wall therebetween, and a tube in fluid communication with second chamber;

passing the blood into the second chamber through the tube;

centrifuging the container for separating the blood into plasma, red blood cells, and buffy coat within the second chamber; and expressing a portion of the separated blood into the first and third chambers from the second chamber through the respective common wall via the fluid communication means.

8. The method of claim 7, further comprising the step of labeling the container so that each chamber bears a similar indicia.

9. The method of claim 7 further comprising the steps of:

providing a channel in fluid communication with a chamber;

allowing a portion of the separated blood to flow in the channel;

sealing the channel; and severing the channel from the chamber.

10. The method of claim 9 wherein the step of severing the channel is accomplished by cutting the container.

* * * * *